(12) United States Patent
Melder et al.

(10) Patent No.: US 10,695,542 B2
(45) Date of Patent: Jun. 30, 2020

(54) DRUG COATED BALLOON

(71) Applicant: Medtronic Vascular, Inc., Santa Rosa, CA (US)

(72) Inventors: Robert Melder, Santa Rosa, CA (US); John Kantor, Healdsburg, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 142 days.

(21) Appl. No.: 15/466,482

(22) Filed: Mar. 22, 2017

(65) Prior Publication Data

US 2017/0281912 A1 Oct. 5, 2017

Related U.S. Application Data

(60) Provisional application No. 62/317,711, filed on Apr. 4, 2016.

(51) Int. Cl.
| | | |
|---|---|---|
| *A61L 29/08* | (2006.01) | |
| *A61L 29/16* | (2006.01) | |
| *A61K 31/17* | (2006.01) | |
| *A61K 31/337* | (2006.01) | |
| *A61M 25/00* | (2006.01) | |
| *A61M 25/10* | (2013.01) | |
| *B05D 7/00* | (2006.01) | |

(52) U.S. Cl.
CPC ............ *A61M 25/10* (2013.01); *A61K 31/17* (2013.01); *A61K 31/337* (2013.01); *A61L 29/085* (2013.01); *A61L 29/16* (2013.01); *A61M 25/0045* (2013.01); *A61M 25/1027* (2013.01); *B05D 7/52* (2013.01); *A61L 2300/416* (2013.01); *A61L 2300/608* (2013.01); *A61L 2300/802* (2013.01); *A61L 2420/08* (2013.01); *A61M 2025/105* (2013.01); *A61M 2025/1081* (2013.01)

(58) Field of Classification Search
CPC ..... A61K 31/17; A61K 31/337; A61L 29/085; A61L 29/16; A61M 25/0045
USPC ........................................................ 604/509
See application file for complete search history.

(56) References Cited

U.S. PATENT DOCUMENTS

| | | | |
|---|---|---|---|
| 5,100,429 A | * | 3/1992 | Sinofsky ................. A61F 2/958 128/DIG. 8 |
| 2010/0185146 A1 | | 7/2010 | Ramzipoor et al. |
| 2010/0233228 A1 | | 9/2010 | Speck |
| 2011/0295200 A1 | * | 12/2011 | Speck ..................... A61L 29/06 604/103.02 |

(Continued)

FOREIGN PATENT DOCUMENTS

| | | |
|---|---|---|
| WO | 2010/079218 A2 | 7/2010 |
| WO | WO2012/039884 | 3/2012 |
| WO | 2013/146381 A1 | 10/2013 |

OTHER PUBLICATIONS

EP17163580.8, Extended European Search Report, dated Aug. 30, 2017, 9pgs.

(Continued)

*Primary Examiner* — Phillip A Gray

(57) ABSTRACT

A balloon catheter includes an inflatable balloon defining an inner and an outer surface. A first biocompatible layer that includes hyaluronic acid is releasably disposed on the outer surface of the balloon. A second drug containing layer is disposed on the first biocompatible layer. The second drug containing layer includes paclitaxel and urea.

19 Claims, 6 Drawing Sheets

(56) References Cited

U.S. PATENT DOCUMENTS

| 2012/0177742 A1* | 7/2012 | McClain ............... A61L 29/085 |
| | | 424/490 |
| 2014/0288497 A1 | 9/2014 | Ewing et al. |
| 2015/0258251 A1 | 9/2015 | Drumheller et al. |

OTHER PUBLICATIONS

Petersen et al., "Development and In Vitro Characterization of Hyaluronic Acid-Based Coatings for Implant-Associated Local Drug Delivery Systems" Journal of Chemistry, vol. 2013, Article ID 587875, 11 pages.

\* cited by examiner

DRUG COATED BALLOON

RELATED APPLICATIONS

This application claims the benefit of U.S. Provisional Patent Application 62/317,711 filed Apr. 4, 2016. The disclosure of which has been herein incorporated by reference in its entirety.

FIELD

The present disclosure relates to, among other things, balloon catheters; and particularly to balloon catheters having a drug coated balloon.

TECHNICAL BACKGROUND

Vascular atherosclerotic lesions that create arterial luminal narrowing are typically treated in angioplasty procedures via catheters provided with a balloon. The catheter is advanced, typically following a guidewire, to an opening within the atherosclerotic lesion of the narrowed artery. Once the balloon has been arranged at the artery narrowing, it may be inflated and deflated, sometimes repeatedly. The inflation, with successive deflation, of the balloon within the artery can reduce the extent of the arterial luminal narrowing, and restore a suitable blood flow.

In many cases, patients develop a new narrowing of the vessel lumen at the intervention point within a few months. Such narrowing, or restenosis, is due to a cell hyperproliferation process, particularly of the vascular smooth muscle cells, probably due to the dilating action caused by the balloon.

Balloons can be coated with a drug having anti-proliferative action to prevent or retard restenosis. Among the drugs usually employed to such aim, paclitaxel (taxol) has proved to be particularly efficient.

However, the majority of solid phase paclitaxel is rapidly cleared from the target site to the distal vasculature, usually occurring within days of treatment. This clearance is thought to be associated with the mechanical interaction of active blood flow and the resulting wall shear stress with the solid phase drug adherent to the vessel wall.

Consequently, the drug dose coated onto the balloon is empirically determined to take this loss into account. However, more efficient retention of drug on the vessel wall at the site of treatment would be beneficial to facilitate lower doses of drug on the balloon and lower drug exposure to distal tissues.

BRIEF SUMMARY

Described herein, among other things, is a balloon catheter comprising an inflatable balloon on which a releasable biocompatible layer is disposed. A second drug-containing layer is disposed on the releasable biocompatible layer. When the balloon is inflated in an artery, the drug-containing layer contacts the artery, and the releasable biocompatible layer may serve to protect deposited solid phase drug from dislodgement for a period of time after the drug is delivered to the artery. For example, when the balloon is inflated the drug may come into contact with the vessel wall, hydrate, and adhere to the intimal tissue of the vessel. Simultaneously, the underlying biocompatible layer may also hydrate and adhere to the intimal tissue such that the drug resides between the biocompatible layer and the tissue. Once the balloon is deflated and withdrawn, blood flow is restored and the biocompatible layer may retard the dislodgement of the drug.

In general, in one aspect, the present disclosure describes a balloon catheter comprising an inflatable balloon defining an interior and an exterior surface. A first biocompatible layer comprising hyaluronic acid is releasably disposed on the exterior surface of the balloon. A second drug containing layer is disposed on the first biocompatible layer. The second drug containing layer comprises paclitaxel and urea.

In embodiments, the paclitaxel and the urea together comprise 90% or more of the weight of the second drug containing layer. In various embodiments, the second drug containing layer consists essentially of urea and paclitaxel.

In embodiments, the first biocompatible layer comprises a sheet wrapped around the balloon. In various embodiments, the sheet has a width substantially equal to the outer diameter of the balloon when the balloon is inflated. The sheet may define a first edge and a second opposing edge along the width of the sheet, wherein the second edge extends beyond the first edge when the sheet is wrapped around the balloon when the balloon is uninflated.

In embodiments, the balloon catheter further comprises a sheath disposed over the balloon to retain the sheet on the balloon.

In general, in another aspect, the present disclosure describes a method comprising inserting a balloon of a balloon catheter into a vessel of a patient, the vessel comprising a vessel wall defining a vessel lumen, wherein the balloon catheter comprises a first biocompatible layer comprising hyaluronic acid releasably disposed on the balloon, and a second drug containing layer disposed on the first biocompatible layer, the second drug containing layer comprising paclitaxel and urea. The balloon is inflated within the vessel to cause the second drug containing layer to contact tissue of the patient. The balloon is deflated leaving the second drug containing layer and the first biocompatible layer in the vessel, wherein the second drug containing layer is in contact with the vessel wall and the first biocompatible layer and is disposed between the vessel wall and the first biocompatible layer.

In embodiments, the paclitaxel and the urea together comprise 90% or more of the weight of the second drug containing layer. In certain embodiments, the second drug containing layer consists essentially of urea and paclitaxel.

In embodiments, the method further comprises advancing the balloon with a sheath disposed over the balloon to a target location within the vessel before inflating the balloon, and retracting the sheath to expose the balloon after the balloon is advanced to the target location, wherein the sheath is retracted prior to inflating the balloon.

In various embodiments, the first biocompatible layer comprises a sheet wrapped around the balloon prior to inflating the balloon, and the sheath retains the sheet on the balloon while the balloon is advanced to the target location of the vessel.

In general, in another aspect, the present disclosure describes a method for coating a medical balloon, comprising disposing a layer comprising hyaluronic acid on an exterior surface of the balloon. A layer comprising paclitaxel and urea is disposed onto the layer comprising hyaluronic acid.

In embodiments, the layer comprising hyaluronic acid consists essentially of hyaluronic acid. In various embodiments, the layer comprising paclitaxel and urea consists essentially of paclitaxel and urea. In embodiments, the layer comprising paclitaxel and urea is disposed on the layer comprising hyaluronic acid prior to the layer comprising hyaluronic acid being disposed on the balloon.

In embodiments, disposing the layer comprising hyaluronic acid on the balloon comprises wrapping a sheet comprising hyaluronic acid around the balloon in an uninflated state. In various embodiments, the sheet may define a first edge and a second opposing edge along the width of the sheet, wherein wrapping the sheet around the balloon comprises overlapping at least a portion of the sheet such that the second edge extends beyond the first edge.

Advantages and additional features of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, in which.

Figure 1:
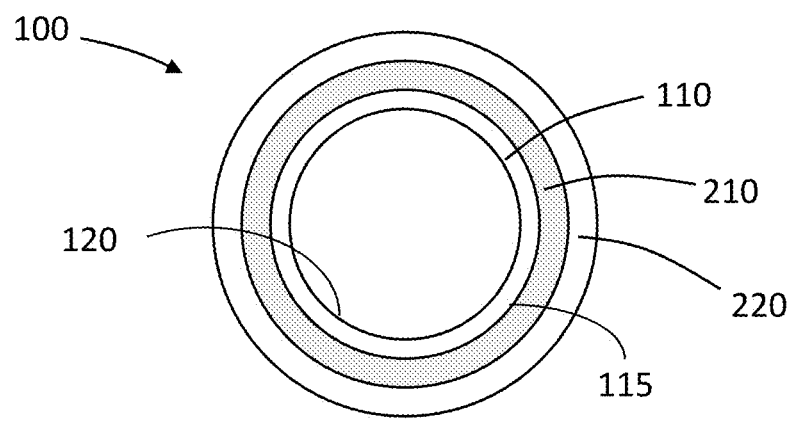
FIG. 1 is a schematic sectional view of an embodiment of a drug-coated balloon.

The schematic drawings are not necessarily to scale.

DETAILED DESCRIPTION

Reference will now be made in greater detail to various embodiments of the subject matter of the present disclosure, some embodiments of which are illustrated in the accompanying drawings. Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

The present disclosure describes, among other things, a balloon catheter on which a first biocompatible layer is disposed and a second drug-containing layer disposed on the first biocompatible layer. When the balloon is inflated, the drug may come into contact with tissue in a patient and may hydrate and adhere to the tissue. The underlying first biocompatible layer may also hydrate and adhere to the tissue such that the drug resides between the first biocompatible layer and the tissue. The first biocompatible layer may serve to protect deposited drug for a period of time after the drug is delivered to the tissue. If the drug does not hydrate well or does not adhere well to the tissue, adherence of the first biocompatible layer to the tissue may serve to retain the drug relative to the tissue.

The first biocompatible layer may be formed from any suitable material or materials. Preferably, the first biocompatible layer is biodegradable and is releasable from the balloon when the balloon is inflated. The entirety of the first biocompatible layer need not release from the balloon, provided that a sufficient amount releases to retard the dislodgement of the drug from the tissue, which may be for example days to months. By way of example, 50% or more of the first biocompatible layer may be released from the balloon when the balloon is inflated at the target tissue site of a patient. For example, between 50% and 95% of the first biocompatible layer may be released from the balloon. In some embodiments, the entirety of first biocompatible layer is released from the balloon.

The first biocompatible layer may be coated on a balloon by, for example, dipping, spraying, or otherwise depositing a solution containing a layer-forming material on the balloon and evaporating a solvent, leaving the first biocompatible layer deposited on the balloon. The first biocompatible layer may be coated on the balloon when the balloon is inflated or folded. If the balloon is folded, the layer-forming material may penetrate under the folds by capillarity action or may be applied by, for example, micro-nozzles under the folds. Preferably, the first biocompatible layer is deposited on the balloon when the balloon is inflated. One or more coatings of a solution comprising the first biocompatible layer-forming material may be applied to the balloon to form the first biocompatible layer.

Alternatively, a sheet comprising the first biocompatible layer may be placed around the balloon. The sheet may be cast or otherwise formed from material comprising the first biocompatible layer-forming material using, for example, film forming processes generally known in the art. The sheet may have a dimension, such as a length, that is larger than, the same size as, or smaller than the length of the balloon about which it is to be placed. Preferably, the sheet has a dimension that is substantially (e.g., within about 10%) equal to the length of the balloon. The sheet may have a dimension, such as a width, that is substantially (e.g., within about 10%) equal to the outer diameter of the balloon when the balloon is fully inflated. Accordingly, when the sheet is released from the balloon upon inflation of the balloon and contact of the sheet with tissue, such as vascular tissue, the sheet may wrap around the entirety of the vascular lumen.

The sheet may be wrapped around a deflated balloon. If the sheet has a width substantially the same as the outer diameter of the fully inflated balloon, a portion of the sheet may overlap another portion of the sheet when the sheet is wrapped around a deflated balloon. For example, the sheet may have a first edge and a second opposing edge along the width of the sheet where the second edge extends beyond the first edge when the sheet is wrapped around the uninflated balloon.

A sheath may be employed to retain the sheet around the balloon when the sheet is tracked within the vasculature. The sheath may be withdrawn prior to inflating the balloon. Alternatively or in addition, the sheet may be folded with the balloon. During tracking the sheet may remain in place relative to the balloon due to the folding of the balloon. The balloon unfolds upon inflation to release the sheet, which may then adhere to the vessel wall, with the second drug containing layer in contact with the vessel wall and disposed between the vessel wall and the first biocompatible layer. In some embodiments, the sheet may be retained in place about the balloon by a stent expandable by the balloon.

The first biocompatible layer, whether a coating or a sheet, may comprise any suitable biocompatible material. Preferably, the biocompatible material is biodegradable. The biocompatible material may be synthetic or natural in origin. If natural in origin, the material may be modified as known in the art to alter rate of biodegradation or other properties such as viscoelastic properties. The biocompatible material may comprise one or more suitable polymers.

Suitable biocompatible polymers include biodegradable polymers such as polyesters, poly(amino acids), copoly (ether-esters), polyalkylenes oxalates, polyamides, poly (iminocarbonates), polyorthoesters, polyoxaesters, polyamidoesters, polyoxaesters containing amido groups, poly (anhydrides), polyphosphazenes, poly-hydroxy acids, poly-α-hydroxy acids, trimethylene carbonate, polyorganophosphazines, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides), polyanhydrides, polysaccharides, and proteins such as gelatin. For example, the first biocompatible layer may comprise one or more of polyhydroxyalkanoates (PHA), polyhydroxybutyrate compounds, and co-polymers and mixtures thereof, poly(glycerol-sebacate), polypeptides, poly-α-hydroxy acid, such as polylactic acid (PLA). By way of further example, the first biocompatible layer may include one or more of polyglycolide (PGA), copolymers of lactide and glycolide (PLGA), polydioxanone, polygluconate, polylactic acid-polyethylene oxide copolymers, alginates, hyaluronic acid.

In some preferred embodiments, the biocompatible material comprises a polysaccharide. The polysaccharide may be cross-linked. For example, the polysaccharide may be chemically crosslinked with glutaraldehyde or another compound having at least two aldehyde groups. By way of another example, crosslinking may be ionic. Ionic cross-linking may be particularly suitable for polysaccharides having acid functional groups, such as glycosaminoglycans. Examples of suitable glycosaminoglycans having acid functional groups include hyaluronic acid, xanthan gum, carrageenan, tragacanth, gellan gum and pectins. Crosslinking may be provided with a biocompatible polyvalent cation such as calcium, magnesium or iron. In some cases a polymer with multiple cationic groups may be utilized.

Preferably, the first biocompatible layer comprises hyaluronic acid. Hyaluronic Acid (HA) is a water soluble high molecular weight (MW) polysaccharide commonly found in normal human tissue, as well as a number of other natural sources. It is biocompatible, non-thrombogenic, highly hydrophilic, hydroscopic, and with a high intrinsic viscosity at high MW and concentration. HA is highly insoluble in most organic solvents and will remain stable during most drug coating processes that include organic solvents. HA can be of various MW, although MWs of greater than or equal to $1\times10^6$ Da are preferred due to a higher degree of chain interaction. In some embodiments the first biocompatible layer consists of or consists essentially of HA. In some embodiments, the first biocompatible layer may include HA mixed with varying amounts of another polymer, such as PVA or amylose or amylopectin and plasticizing agent such as glycerol, to adjust visco-elastic properties. In some embodiments, the HA is cross-linked to increase stability of the resulting HA layer or alter the rate of degradation.

Another advantage of HA is its intrinsic antithrombotic properties. When used for treatment of, for example, restenosis, HA may inhibit thrombus formation at the treatment site in response to barometric trauma induced by the interventional procedure, such as balloon inflation, to reduce the extent of the arterial luminal narrowing. Further, the HA layer may retard blood flow into a vascular dissection resulting from the interventional procedure, thus stabilizing the dissection and promoting healing. The HA may also retard macrophage and inflammatory cell infiltration into the treatment site, reducing local neointimal responses.

In some embodiments the first biocompatible layer is formulated to substantially degrade over a period of one day to one month after being delivered to tissue via the balloon. For example, the first biocompatible layer may substantially degrade over days to weeks after delivery. The first biocompatible layer may retain the drug adjacent to the tissue at the delivery site until the drug is adsorbed or until the first biocompatible layer degrades.

The thickness of the first biocompatible layer may affect the rate of degradation of the layer once released from the balloon. The thickness may be selected to achieve a desired time for degradation. The first biocompatible layer may be of any suitable thickness. For example, the first biocompatible layer may have a thickness of less than 50 µm or less than 30 µm, such from 0.1 µm to 50 µm or from 1 µm to 30 µm.

The first biocompatible layer, whether in a coating or as a sheet, may be placed directly on the balloon, or one or more intervening layers may be disposed between the balloon and the first biocompatible layer. For example, in some instances where a sheet comprises the first biocompatible layer, a lubricant may be placed between the sheet and the balloon to facilitate release of the sheet from the balloon. Preferably, the first biocompatible layer is placed directly on the balloon without any intervening layers.

The first biocompatible layer may be placed on a balloon of any suitable balloon catheter. The balloons may be compliant, semi-compliant or non-compliant. The balloons may be formed from any suitable material. For example, the balloons may be formed of polyamides, polyethylene terephathalate (PET), polyurethane, latex, silicone, polyethylene (PE), polypropylene (PP), polyetherimide (PEI), polytetrafluoroethylene (PTFE), ethylene tetrafluoroethylene (ETFE), fluorinated ethylene propylene (FEP), polyoxymethylene (POM), polybutylene terephthalate (PBT), polyether-block-ester, polyvinylchloride (PVC), polyether-block-amide, polyetheretherketone (PEEK), polyimide (PI), polyphenylene sulfide (PPS), polyphenylene oxide (PPO), poly(ethylene naphthalenedicarboxylate) (PEN), polysulfone, perfluoro(propyl vinyl ether) (PFA), or mixtures, combinations, copolymers thereof, and the like.

The balloon will typically have a length of at least 1 cm, preferably being in a range from about 1.5 cm to 25 cm, and may have inflated diameters in a range from 1.5 mm to about 10 mm, for instance 4 mm to 7 mm, but may be of any suitable size.

Any one or more suitable drug may be disposed on the first biocompatible layer. The drug layer preferably is a distinct layer from the first biocompatible layer and not intermixed with the first biocompatible layer. In some preferred embodiments, the drug-containing layer is polymer-free.

Non-limiting examples of drugs that may be employed include anti-restenosis agents, antiproliferative agents, antibiotic agents, antimitotic agents, antiplatelet agents, alkylating agents, platinum coordination complexes, hormones, anticoagulants, fibrinolytic agents, antimigratory agents, antisecretory agents, anti-inflammatory agents, indole acetic acids, indene acetic acids, immunosuppressive agents, angiogenic agents, angiotensen receptor blockers, nitric oxide donors, anti-sense oligonucleotides, cell cycle inhibitors, mTOR inhibitors, growth factor receptor signal inhibitors, transduction kinase inhibitors, retenoids, cyclin/CDK inhibitors, HMG co-enzyme reductase inhibitors, and protease inhibitors.

Unless content clearly dictates otherwise, general reference to a drug in the present disclosure includes reference to salts of the drug, hydrates of the drug, polymorphs of the drug, isomers of the drug (including constitutional isomers and stereoisomers such as enantiomers and diasteriomers), and the like.

In some embodiments, the drug-containing layer includes one or more polymorphs of a drug. Polymorphs may have different solubilities or crystal forms. Polymorphs may have characteristics that affect tissue uptake of the drug at the delivery site or dissolution rate in bodily fluids. The polymorph(s) in the drug-containing layer may be selected to facilitate a particular therapeutic objective.

The drug-containing layer may include drug particles having any suitable size profile. Preferably, the particulate size profile facilitates uptake by the tissue. Very small particles, such as particles less than 1 µm in size, may be taken up directly into the arterial tissue. In some embodiments the drug-containing layer includes a drug in a particulate form that has a particle size in a range from 0.01 µm to 20.0 µm. Multi-modal ranges, prepared, e.g. by mixing two or more sets of different size ranges may be used in some cases to provide a desired bioavailability profile over time. For example, smaller crystals will more readily dissolve and enter the tissue for immediate effect, while larger crystals will dissolve at a much slower rate enabling longer drug persistence.

The drug-containing layer may include drug in crystalline or amorphous form. In some embodiments, the drug-containing layer includes a drug in both an amorphous and a crystalline form. In some embodiments, the drug-containing layer may include a drug in more than one crystalline form.

The drug-containing layer preferably comprises one or more drugs in a therapeutically effective amount. As used herein, "therapeutically effective amount" means a drug amount capable of inducing a therapeutic or preventive effect against the disease being treated or prevented. For example, if the disease being treated or prevented is restenosis of vascular tissue, the one or more drugs present in the drug-containing layer may be present in an amount effective to treat or prevent restenosis of the treated vascular tissue in the patient.

The drug-containing layer may comprise one or more drugs in any suitable density. For example, the drug may be present in the drug-containing layer at a density from about 0.1 µg/mm$^2$ to about 100 µg/mm$^2$, such as between about 0.25 µg/mm$^2$ to about 20 µg/mm$^2$. By way of example, the drug-containing layer may include paclitaxel in an amount ranging from 1 µg/mm$^2$ to 20 µg/mm$^2$, preferably between 2 µg/mm$^2$ and 7 µg/mm$^2$, more preferably between 3 µg/mm$^2$ and 5 µg/mm$^2$.

In some embodiments, the drug-containing layer comprises one or more of zotarolamus, sirolimus, dexamethasone and paclitaxel.

Preferably, the drug-containing layer comprises paclitaxel and is used to treat restenosis. Preferably, at least some or all of the paclitaxel is in anhydrous crystalline form. Preferably, the drug containing layer provides for immediate release and bioavailability of a therapeutically effective amount of paclitaxel when the balloon is expanded and the drug-containing layer contacts tissue at the site of intervention.

As used herein, "an immediate release and bioavailability" means a release from the balloon surface in periods of time ranging between 1 second and 1.5 minutes, preferably between 20 seconds and 1 minute, and an absorption by the vascular tissue in periods of time ranging between 1 second and 25 minutes, preferably between 20 seconds and 25 minutes.

As used herein, "site of intervention" means, when describing use in a blood vessel, the section of the blood vessel treated directly with a catheter balloon described herein, and the adjacent portion in the tissues of which the post-procedure presence of paclitaxel can be detected. Generally, such section will extend for 2 to 10 mm down- and upstream of the contact section with the balloon. The vessel is comprised of a vessel wall defining a vessel lumen.

As used herein paclitaxel in "anhydrous crystalline form" means paclitaxel essentially free from water of crystallization. Anhydrous crystalline paclitaxel may be obtained by direct crystallization, or hot and/or vacuum drying, of a hydrated or solvated hydrated form.

This crystalline form of paclitaxel can be obtained by dissolving paclitaxel in an aqueous solvent, by completely or partially wetting the first biocompatible layer with such solution, and by letting the solvent evaporate, naturally or by hot and/or vacuum drying, to the formation of a crystalline layer having a white, homogeneous, or partially inhomogeneous appearance. As the aqueous solvent, a mixture of solvents selected from acetone/ethanol/water, tetrahydrofuran/water, methanol/water, acetone/water, ethanol/water, acetonitrile/water, DMF/water is preferably used. More preferably, the solvent is a 9:1 tetrahydrofuran/water mixture or a tetrahydrofuran/water mixture with ratios ranging between 9.5:0.5 and 65:35, or an acetone/ethanol/water mixture in which the organic solvent is present in amounts not less than 50% by volume relative to water.

In some embodiments, the drug-containing layer comprises all crystalline paclitaxel or a mixture of amorphous and crystalline paclitaxel. For example, the fraction of the paclitaxel that is amorphous may be from 0% to 25%, such as about 1% to about 5%, based on total paclitaxel weight. The fraction of the paclitaxel that is crystalline may be, for example, from 1% to 100%, such as from about 75% to about 100%, based on the total paclitaxel weight. The fraction of the paclitaxel that is anhydrous may be 5% to 100%.

Preferably, a drug-containing layer comprising paclitaxel also comprises urea. The presence of urea in a paclitaxel-containing layer may promote the release of the paclitaxel.

Paclitaxel may be dissolved in an appropriate solvent in the presence of urea and coated on the first biocompatible layer. Urea may be used in any suitable amount, such as from 1 mg per mL to 100 mg per mL solvent, preferably from 4 mg per mL to 10 mg per mL solvent, more preferably about 7 mg per mL solvent. In some preferred embodiments, the paclitaxel and urea comprises at least 90% of the weight of the drug-containing layer, such as at least 95% or 99% of the weight of the drug containing layer.

In general, a drug-containing layer may be disposed on the first biocompatible layer in any suitable manner. For example, a solution comprising the drug, such as the solvent containing paclitaxel or paclitaxel and urea, can be coated on the first biocompatible layer in any suitable manner. For example, a balloon previously coated with the first biocompatible layer can be dipped in the drug-containing solution, the drug-containing solution can be sprayed on the first biocompatible layer, the drug-containing solution can be deposited on the first biocompatible layer with, for example, a syringe, micropipette, or other similar dispensing device.

The drug-containing solution may be applied to the first biocompatible layer after the first biocompatible layer is disposed on or about the balloon, or may be applied to a first biocompatible layer sheet, which may be disposed about the balloon after the drug-containing solution has been applied to the sheet.

If the first biocompatible layer is disposed on the balloon, the drug-containing solution may be applied when the balloon is inflated, or in a folded condition. If applied when the balloon is in the folded condition, the drug-containing solution may penetrate under the folds by capillarity action, or may be applied by, for example, micro-nozzles under the folds.

One or more coatings of the drug-containing solution may be applied to the first biocompatible layer. The solvent may be allowed to evaporate under ambient conditions, under heated conditions, under vacuum drying, or heating and vacuum drying. The first biocompatible layer may be fully or partially coated with the drug-containing layer.

In preferred embodiments, a balloon catheter comprises a first biocompatible layer comprising hyaluronic acid and a drug-containing layer comprising paclitaxel. Preferably, the drug-containing layer further comprises urea.

Referring now to FIG. 1, a cross-section of an inflated drug-coated balloon 100 is shown. The drug-coated balloon 100 includes a balloon wall 110 having an outer surface 115 on which, or about which, a first biocompatible layer 210 is coated or placed, and an inner surface 120. A second drug-containing layer 220 is disposed on the first biocompatible layer 210.

Figure 2:
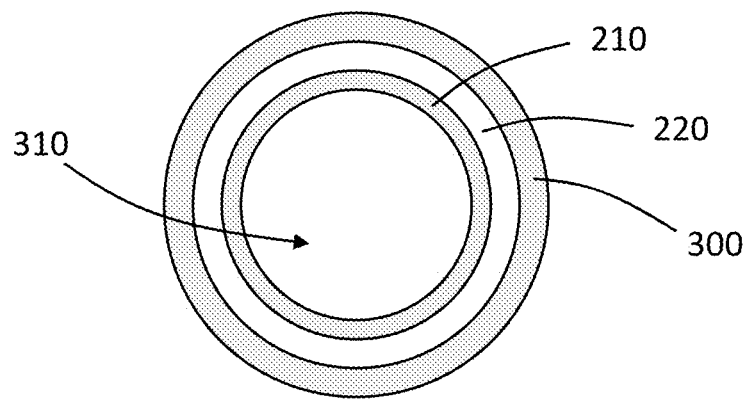
FIG. 2 is a schematic sectional view of an embodiment of an artery following delivery of a drug-containing layer and a biocompatible layer from a balloon catheter.

Referring now to FIG. 2, a cross-section of a vessel 300, such as an artery, following delivery the first biocompatible layer 210 and the second drug-containing layer 220, such as from a drug-coated balloon as depicted in FIG. 1, is shown. After delivery, the second drug-containing layer 220 is disposed between the vessel 300 wall and the first biocompatible layer 210. Blood may flow through the lumen 310 of the vessel 300. The first biocompatible layer 210 protects drug in the second drug-containing layer 220 from being dislodged from the vessel 300 due to the flow of blood.

Figure 3A:
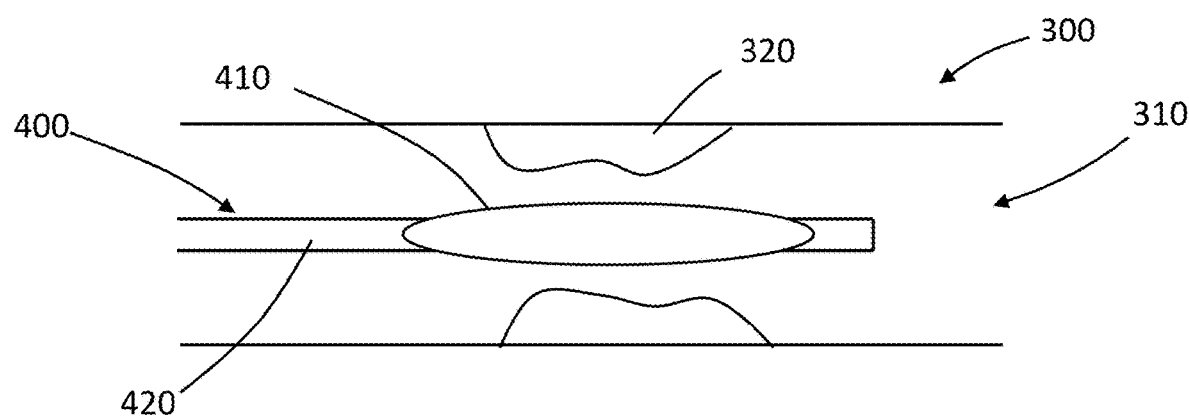
FIGS. 3A-G are schematic sectional views illustrating an embodiment of a process for treating narrowing of an artery.
Figure 3B:
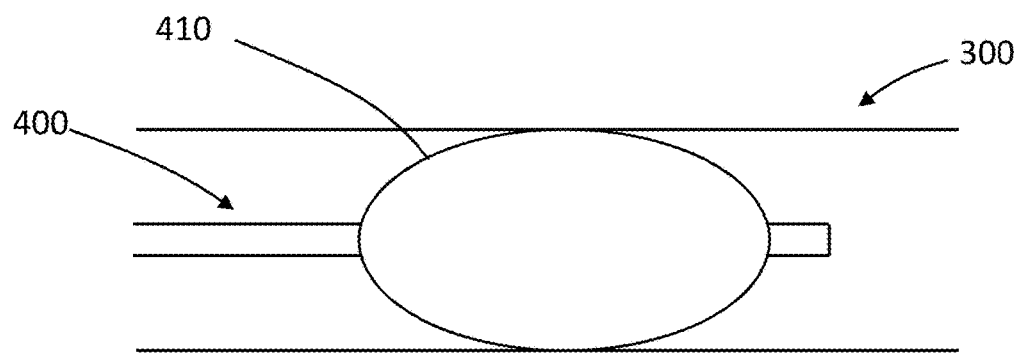
Figure 3C:
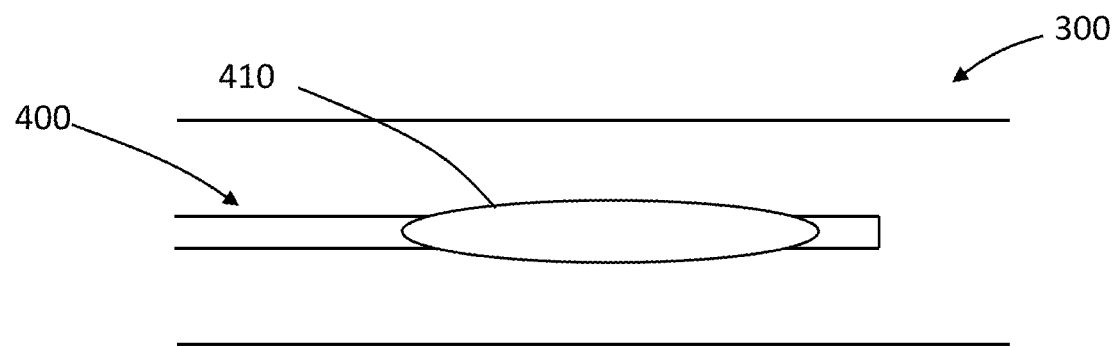
Figure 3D:
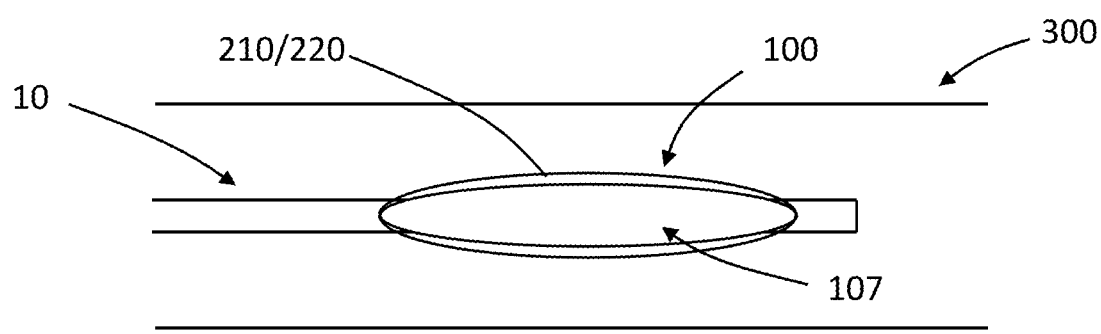
Figure 3E:
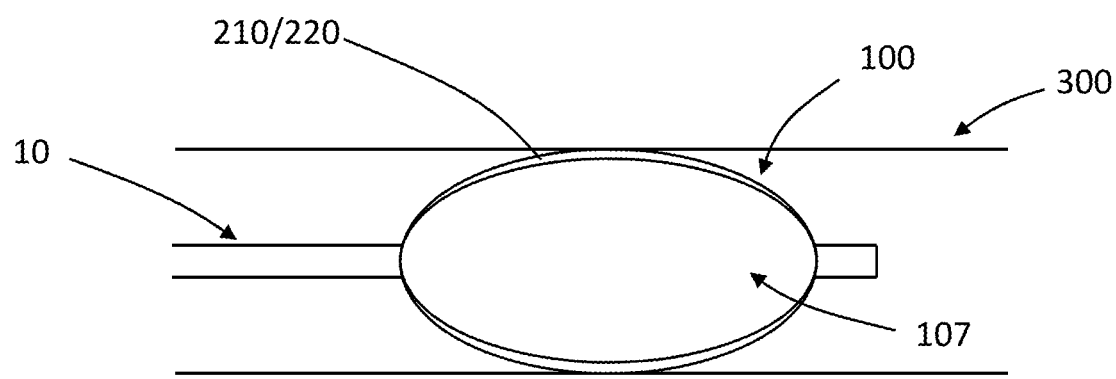
Figure 3F:
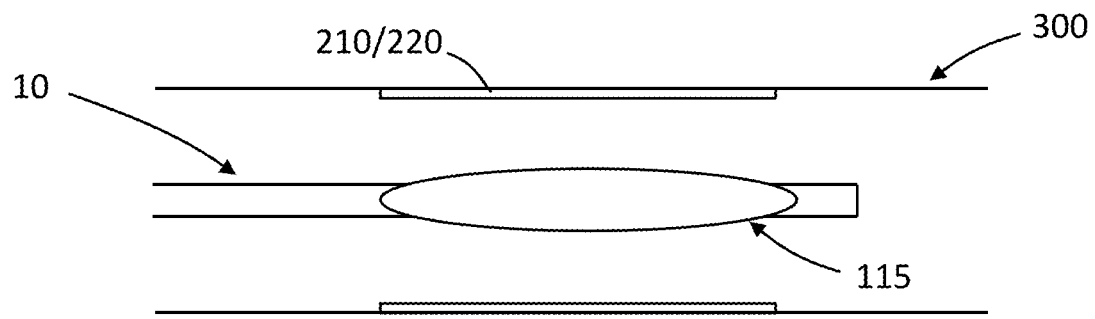
Figure 3G:
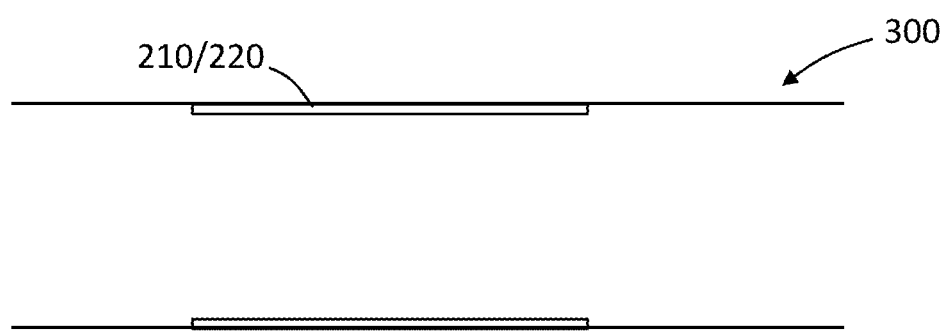

Referring now to FIGS. 3A-G, a series of steps in a method for treatment of a narrowing of an artery and/or restenosis is shown. In the depicted embodiment, a balloon catheter 400 is advanced through a lumen 310 of a vessel 300, such as an artery, until a balloon 410 is aligned with a narrowing 320 of the vessel 300 (FIG. 3A). The narrowing may be caused by a lesion, such as an atherosclerotic lesion, or restenosis from a previous treatment. The balloon 410 is inflated (FIG. 3B) to expand the vessel 300 in the area of the narrowing. The balloon 410 is deflated (FIG. 3C) and the balloon catheter 400 is removed from the artery once the narrowing has been appropriately enlarged. A drug-coated balloon catheter 10 having a drug-coated balloon 100, such as a balloon depicted in FIG. 1, is advanced in the lumen 310 of the vessel 300 to the location where the narrowing was treated (FIG. 3D). The drug-coated balloon 100 has a first biocompatible layer 210 and second drug-containing layer 220. The drug-coated balloon 100 is inflated so that the drug containing layer 220 contacts an inner surface of the wall of the artery (FIG. 3E). The balloon 100 may be inflated through introduction of fluid into an interior 107 of the balloon through for example a lumen (not shown) of the catheter that is in communication with the interior of the balloon. Drug in the drug containing layer 220 may wet and adhere to the vessel 300, such as an artery. The first biocompatible layer 210 may also wet and adhere to the wall of the artery 300, such that when the balloon is deflated (FIG. 3F) the first biocompatible layer 210 and second drug-containing layer 220 remain attached to the vessel 300, and are released from an outer surface 115 of the balloon. The balloon catheter 10 may then be removed from the vessel 300.

Figure 4A:
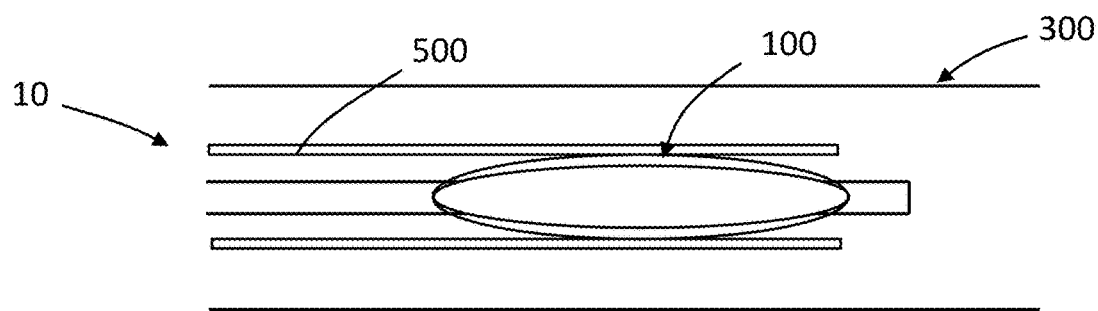
FIGS. 4A-C are schematic sectional views illustrating an embodiment of a process for delivering a drug-coated balloon to an artery with a balloon catheter having a sheath.
Figure 4B:
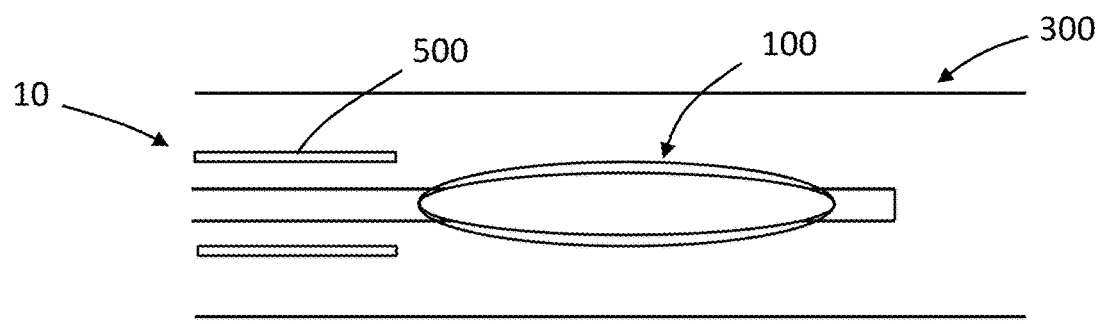
Figure 4C:
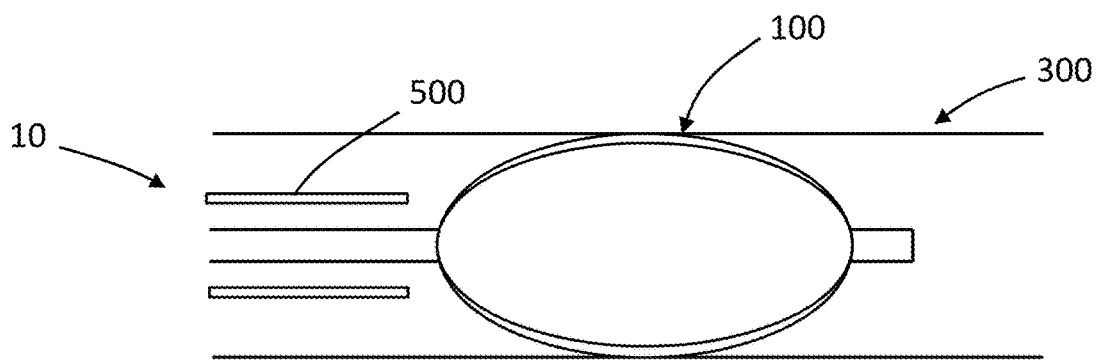

Referring now to FIGS. 4A-C, a drug coated balloon 100 having a retractable sheath 500 may be employed to treat a vessel 300. The drawings in FIGS. 4A-C may correspond generally to the steps depicted in FIGS. 3C-E, respectively. In FIG. 4A the balloon catheter 10 is advanced in the vessel 300 to the location where the narrowing was treated. The sheath 500 may be retracted (FIG. 4B) and the drug coated balloon 100 inflated (FIG. 4C) such that the second drug-containing layer 220 contacts the wall of the vessel 300. A sheath may preferably be employed in embodiments where the first biocompatible layer 210 and second drug-containing layer 220 are present in a sheet wrapped around the balloon.

Figure 5:
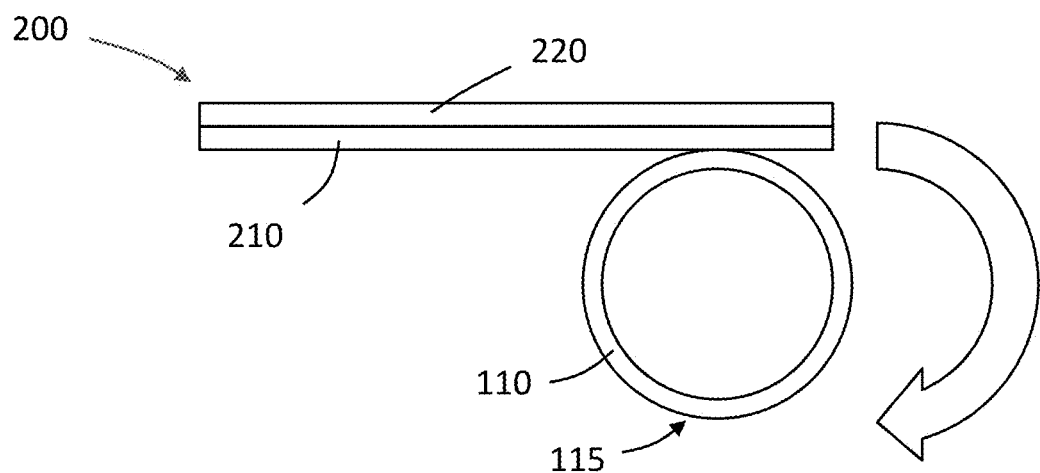
FIG. 5 is a schematic sectional view illustrating wrapping of a sheet containing a first biocompatible layer and a second drug-containing layer around a balloon.

Referring now to FIG. 5, a schematic illustration of a process for wrapping a sheet 200 containing a first biocompatible layer 210 and a second drug-containing layer 220 around an outer surface 115 of a balloon 110 is shown. Preferably, the balloon 110 is deflated and folded (folds not shown). The sheet 200 is wrapped around the balloon 110 such that the first biocompatible layer 210 faces the balloon 110 and the second drug containing layer 220 faces away from the balloon.

Figure 6:
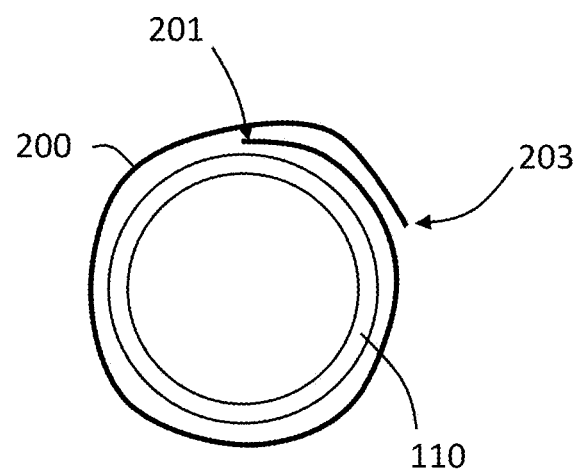
FIG. 6 is a schematic sectional view illustrating a sheet wrapped around a deflated balloon.

Referring now to FIG. 6, an embodiment of a sheet 200 wrapped around a deflated and folded balloon 110 (folds not shown) is depicted. The sheet 200 has a first edge 201 and an opposing second edge 203 along the width of the sheet. At least a portion of the sheet overlaps another portion of the sheet such that the second edge 203 extends beyond the first edge 201. When inflated, the outer diameter of the folded balloon 110 is preferably substantially the same as the width of the sheet 200.

While described herein mainly in terms of treatment of lesions or restenosis in arteries, the balloon catheters described herein may be useful for treating other diseases in other passageways. For example, the balloon catheters described herein may be used in veins, coronary arteries, renal arteries, peripheral arteries including illiac arteries, arteries of the neck and cerebral arteries, and may also be advantageously employed in other body structures, including but not limited to arteries, veins, biliary ducts, urethras, fallopian tubes, bronchial tubes, the trachea, the esophagus and the prostate. Further, while the method of treatment has been described as first dilating the vessel with a non-drug coated balloon (e.g., FIGS. 3A-3C), the vessel maybe treated in the first instance with the drug coated balloon of the present disclosure (i.e., without pre-dilating the vessel with a non-drug coated balloon).

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. As used in this specification and the appended claims, the term "or" is generally employed in its sense including "and/or" unless the content clearly dictates otherwise. The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. A balloon catheter comprising:
   an inflatable balloon defining an inner surface and an outer surface;
   a first biocompatible layer comprising hyaluronic acid releasably disposed on the exterior surface of the balloon; and
   a second drug containing layer disposed on the first biocompatible layer, the second drug containing layer comprising paclitaxel and urea.

2. A balloon catheter according to claim 1, wherein the paclitaxel and the urea together comprise 90% or more of the weight of the second drug containing layer.

3. A balloon catheter according to claim 1, wherein the second drug containing layer consists essentially of urea and paclitaxel.

4. A balloon catheter according to claim 1, wherein the first biocompatible layer comprises a sheet wrapped around the balloon.

5. A balloon catheter according to claim 4, wherein the sheet has a width substantially equal to the outer diameter of the balloon when the balloon is inflated.

6. A balloon catheter according to claim 4, wherein the sheet defines a first edge and a second opposing edge along the width of the sheet, wherein the second edge extends beyond the first edge when the sheet is wrapped around the balloon when the balloon is uninflated.

7. A balloon catheter according claim 4, further comprising a sheath disposed over the balloon to retain the sheet on the balloon.

8. A method comprising:
   inserting a balloon of a balloon catheter in a vessel of a patient, the vessel comprising a vessel wall defining a vessel lumen, the balloon catheter comprising a first biocompatible layer comprising hyaluronic acid releasably disposed on the balloon, and a second drug containing layer disposed on the first biocompatible layer, the second drug containing layer comprising paclitaxel and urea;
   inflating the balloon within the vessel to cause the second drug containing layer to contact tissue of the patient; and
   deflating the balloon leaving the second drug containing layer and the first biocompatible layer in the vessel, wherein the second drug containing layer is in contact with the vessel wall and the first biocompatible layer and is disposed between the vessel wall and the first biocompatible layer.

9. A method according to claim 8, wherein the paclitaxel and the urea together comprise 90% or more of the weight of the second drug containing layer.

10. A method according to claim 8, wherein the second drug containing layer consists essentially of urea and paclitaxel.

11. A method according to claim 8, further comprising advancing the balloon with a sheath disposed over the balloon to a target location within the vessel before inflating the balloon, and
    retracting the sheath to expose the balloon after the balloon is advanced to the target location, wherein the sheath is retracted prior to inflating the balloon.

12. A method according to claim 11, wherein the first biocompatible layer comprises a sheet wrapped around the balloon prior to inflating the balloon and wherein the sheath retains the sheet on the balloon while the balloon is advanced to the target location of the vessel.

13. A method for coating a medical balloon, comprising:
    disposing a layer comprising hyaluronic acid on an outer surface of the balloon; and
    disposing a layer comprising paclitaxel and urea onto the layer comprising hyaluronic acid.

14. A method according to claim 13, wherein the layer comprising hyaluronic acid consists essentially of hyaluronic acid.

15. A method according to claim 13, wherein the paclitaxel and the urea together comprise 90% or more of the weight of the layer comprising paclitaxel and urea.

16. A method according to claim 13, wherein the layer comprising paclitaxel and urea consists essentially of paclitaxel and urea.

17. A method according to claim 13, where the layer comprising paclitaxel and urea is disposed on the layer comprising hyaluronic acid prior to the layer comprising hyaluronic acid being disposed on the balloon.

18. A method according to claim 13, wherein disposing the layer comprising hyaluronic acid on the balloon comprises wrapping a sheet comprising hyaluronic acid around the balloon in an uninflated state.

19. A method according to claim 18, wherein the sheet defines a first edge and a second opposing edge along the width of the sheet, wherein wrapping the sheet around the balloon comprises overlapping at least a portion of the sheet such that the second edge extends beyond the first edge.

* * * * *